(12) United States Patent
Tang et al.

(10) Patent No.: US 12,016,775 B2
(45) Date of Patent: *Jun. 25, 2024

(54) HEART VALVE DELIVERY SYSTEM AND METHOD WITH ROTATIONAL ALIGNMENT

(71) Applicants: Icahn School of Medicine at Mount Sinai, New York, NY (US); The Trustees Of Columbia University In The City Of New York, New York, NY (US)

(72) Inventors: Gilbert H. L. Tang, New York, NY (US); Vinayak Bapat, New York, NY (US); Susheel K. Kodali, Hastings On Hudson, NY (US)

(73) Assignees: The Trustees of Columbia University in the City of New York, New York, NY (US); Icahn School of Medicine at Mount Sinai, New York, NY (US)

( * ) Notice: Subject to any disclaimer, the term of this patent is extended or adjusted under 35 U.S.C. 154(b) by 13 days.

This patent is subject to a terminal disclaimer.

(21) Appl. No.: 17/590,571

(22) Filed: Feb. 1, 2022

(65) Prior Publication Data

US 2022/0362017 A1    Nov. 17, 2022

Related U.S. Application Data

(63) Continuation of application No. 16/944,818, filed on Jul. 31, 2020, now Pat. No. 11,273,038, which is a
(Continued)

(51) Int. Cl.
| | |
|---|---|
| *A61F 2/24* | (2006.01) |
| *A61F 2/95* | (2013.01) |
| *A61B 17/00* | (2006.01) |

(52) U.S. Cl.
CPC .......... *A61F 2/2436* (2013.01); *A61F 2/2466* (2013.01); *A61F 2/9517* (2020.05);
(Continued)

(58) Field of Classification Search
CPC .... A61F 2/2436; A61F 2/2409; A61F 2/2418; A61F 2/2403; A61F 2/2466
See application file for complete search history.

(56) References Cited

U.S. PATENT DOCUMENTS

| | | |
|---|---|---|
| 6,168,616 B1 | 1/2001 | Brown, III |
| 9,168,136 B2 | 10/2015 | Yang et al. |

(Continued)

FOREIGN PATENT DOCUMENTS

| | | |
|---|---|---|
| AU | 2017214672 B2 | 8/2017 |
| WO | 2008125153 A1 | 10/2008 |

OTHER PUBLICATIONS

International Search Report cited in corresponding International Application No. PCT/US19/50231 dated Nov. 25, 2019, 2 pages.

*Primary Examiner* — Tuan V Nguyen
(74) *Attorney, Agent, or Firm* — BakerHostetler

(57) ABSTRACT

A delivery system for a transcatheter heart valve (THV) to a subject is provided, the delivery system includes a delivery catheter housing the THV therein; an elongated member for receiving the THV thereon and having an accessory extending from the distal portion thereof, the accessory comprising a plurality of components for alignment with commissures of the THV during delivery of the THV, and a rotational member connected to the elongated member to rotate the accessory and THV together to align with a native or bioprosthetic valve commissure or valve leaflet at a desired angle.

18 Claims, 15 Drawing Sheets

Related U.S. Application Data continuation of application No. PCT/US2019/050231, filed on Sep. 9, 2019.

(60) Provisional application No. 62/728,346, filed on Sep. 7, 2018.

(52) U.S. Cl.
CPC ........... *A61B 2017/00243* (2013.01); *A61B 2017/00367* (2013.01); *A61F 2210/0014* (2013.01); *A61F 2250/0098* (2013.01)

(56) References Cited

U.S. PATENT DOCUMENTS

| | | | |
|---|---|---|---|
| 2002/0055767 A1* | 5/2002 | Forde | A61F 2/962 623/1.11 |
| 2004/0210298 A1 | 10/2004 | Rabkin et al. | |
| 2008/0188928 A1* | 8/2008 | Salahieh | A61M 25/0054 623/2.11 |
| 2012/0197193 A1* | 8/2012 | Krolik | A61B 5/6853 604/99.04 |
| 2012/0271411 A1* | 10/2012 | Duhay | A61F 2/2418 623/2.11 |
| 2013/0110227 A1 | 5/2013 | Quadri et al. | |
| 2013/0310923 A1 | 11/2013 | Kheradvar et al. | |
| 2014/0067037 A1 | 3/2014 | Fargahi | |
| 2014/0074227 A1 | 3/2014 | Tabor | |
| 2015/0142101 A1 | 5/2015 | Coleman et al. | |
| 2016/0228240 A1 | 8/2016 | Olson et al. | |
| 2017/0156858 A1 | 6/2017 | Straubinger et al. | |
| 2018/0078370 A1 | 3/2018 | Kovalsky et al. | |

\* cited by examiner

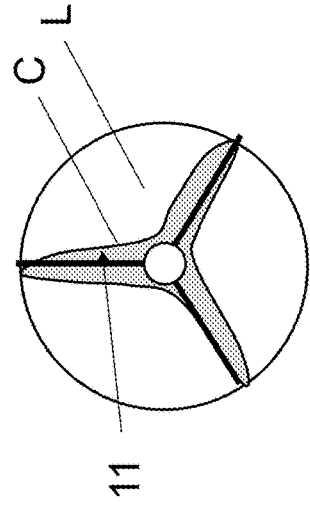
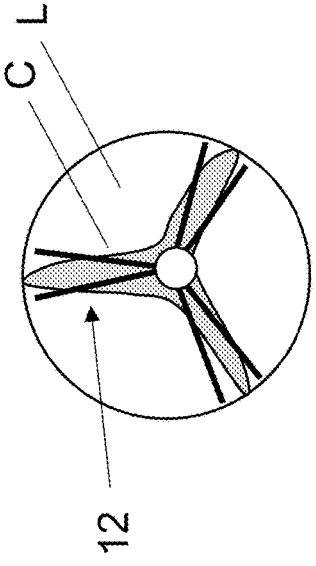
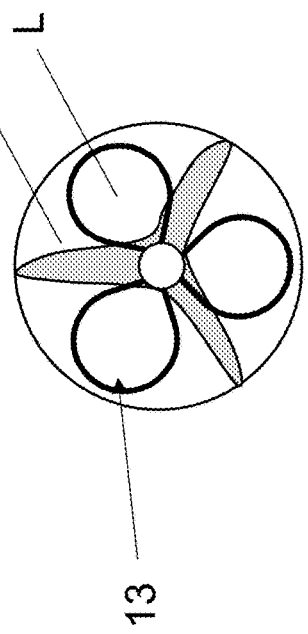
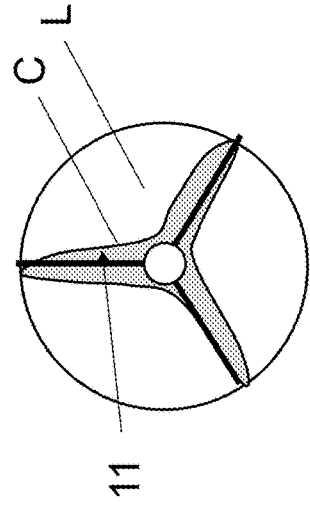
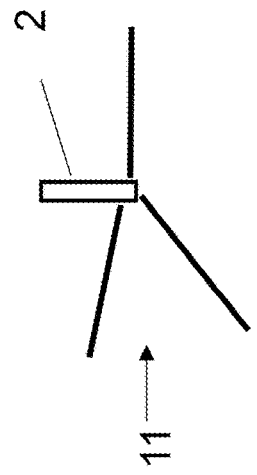
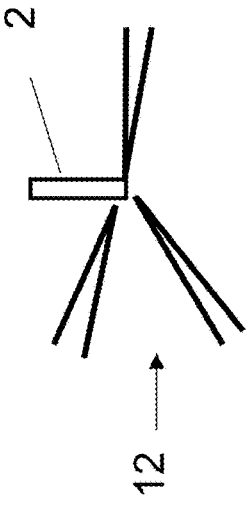

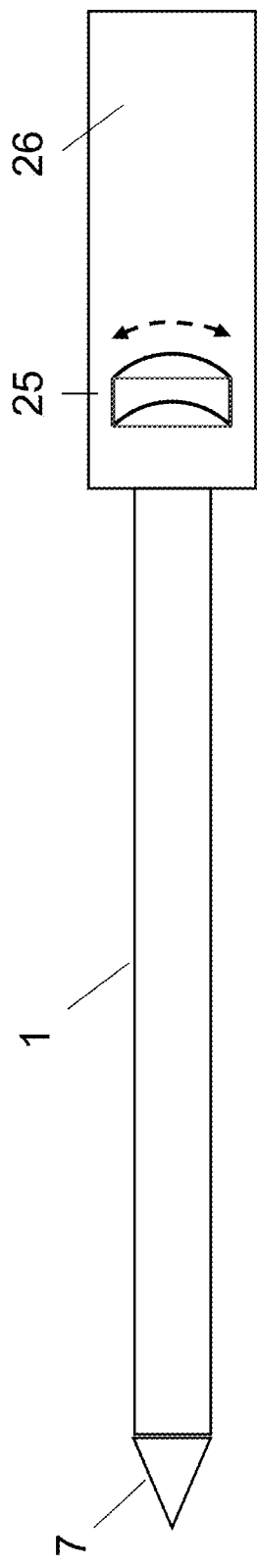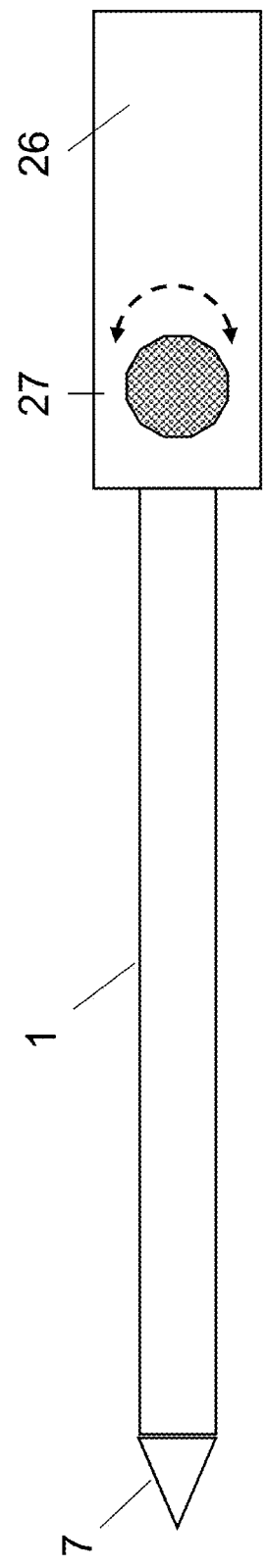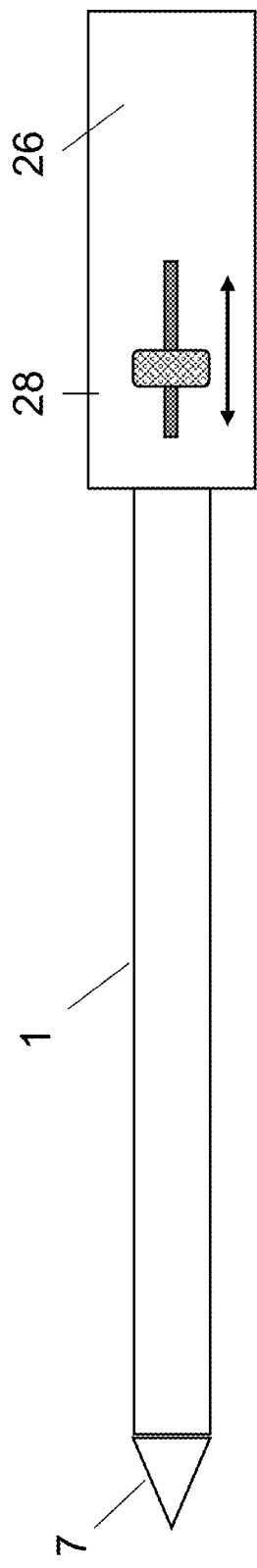

HEART VALVE DELIVERY SYSTEM AND METHOD WITH ROTATIONAL ALIGNMENT

CROSS-REFERENCE TO RELATED APPLICATIONS

The present application is a Continuation of U.S. application Ser. No. 16/944,818, filed Jul. 31, 2020 which is a Continuation of International Application No. PCT/US19/50231, filed Sep. 9, 2019 which claims priority to U.S. Provisional Application 62/728,346, filed Sep. 7, 2018, the entirety of which are incorporated herein by reference.

FIELD

A method and apparatus configured for delivery and implantation of a prosthetic heart valve in a native or prosthetic heart valve.

BACKGROUND

Transcatheter heart valve (THV) replacement in failing native and bioprosthetic valves are becoming increasingly common. THV replacement of native and bioprosthetic aortic, mitral, tricuspid and pulmonic valves has been successfully performed. Transcatheter aortic valve replacement (TAVR) is becoming the preferred treatment in patients with symptomatic severe aortic stenosis and results on comparing surgical vs transcatheter AVR in low risk patients will be available in 2019. Predicted market growth for TAVR to treat severe aortic stenosis is significant. In younger, low risk patients, the long-term durability of TAVR remains unknown, and a significant number of these patients have or will develop significant coronary artery disease, requiring diagnostic and therapeutic interventions. One of the major difference between surgical aortic valve replacement and TAVR is, in surgery the valves are always aligned to native commissures and hence mimic the physiological opening and closing and may influence durability and function. Early evidence has pointed to the fact that, commissural alignment may also influence function of the THV after TAVR. Further, coronary access after TAVR is known to be more difficult than after surgical aortic valve replacement. This is due to the presence of native aortic valve leaflets, the THV frame occupying the aortic root and in some patients due to presence of commissure in front of the coronary ostia. Published case series have shown that coronary angiography and PCI after TAVR are more challenging, requiring more radiation exposure and IV contrast. In urgent or emergency situation such as acute myocardial infarction, the issue of timely coronary access after TAVR is critical to life and death. By aligning the THV commissures to the native commissures, there is a likelihood that there will be better function but more importantly easier access to the coronary ostia. Currently, there is no predictable and consistent method of aligning the THV neo-commissures with the native or bioprosthetic aortic valve commissures with help of a delivery system.

Methods have been developed to split the native or bioprosthetic aortic valve leaflet to facilitate coronary reaccess or avoid coronary obstruction during TAVR. However, if a THV commissure is placed facing the coronary ostium, such a method would not be feasible. This speaks to the importance of developing a device that can align the THV commissures to native commissures.

A delivery system that can consistently deliver a THV to the native or bioprosthetic aortic valve with the neo-commissures aligned with the native or bioprosthetic aortic valve commissures is needed, since it would reduce the risk of neo-commisural tab interference with coronary orifices, making coronary reaccess after TAVR less difficult.

The ability for a delivery system to deliver and help align a THV to native or bioprosthetic valve extends beyond the aortic valve. The ability to deliver and deploy a THV in a native mitral valve with calcification, bioprosthetic pulmonic, mitral and tricuspid valve with specific angle of alignment between neo-commissures and bioprosthetic valve commissures may help improve THV frame expansion and anchor against the bioprosthesis. There may also be hemodynamic reasons of aligning neo-commissures with native and bioprosthetic valve commissures in a specific angle.

SUMMARY

A delivery system for a transcatheter heart valve (THV) to a subject is provided, the delivery system includes a delivery catheter housing the THV therein; an elongated member for receiving the THV thereon and having an accessory extending from the distal portion thereof, the accessory comprising a plurality of components for alignment with commissures of the THV during delivery of the THV, and a rotational member connected to the elongated member to rotate the accessory and THV together to align with a native or bioprosthetic valve commissure or a valve leaflet at a desired angle. In some embodiments, the THV is adapted for placement at the aortic valve, the mitral valve or the tricuspid valve.

In some embodiments, the components of the accessory include a plurality of radially outwardly extending projections. The components are useful to identify the THV neo-commissures or sinuses.

In some embodiments, the projections are disposed at a distal portion of the THV during delivery of the THV. In some embodiments, the projections are disposed at a distal portion of the THV during delivery of the THV.

In some embodiments, the components are atraumatic filamentous projections. In some embodiments, the components are loop-shaped projections. The components can include radiopaque components, e.g., to aid in identifying the orientation of the visible components and the THV under fluoroscopy. They may also contain materials to be distinctively visible on echocardiography to aid in THV rotational alignment and deployment.

In some embodiments, the rotational member includes a rotational wheel positioned on a proximal handle portion. In some embodiments, the rotational member includes a thumb slide positioned on a proximal handle portion. The delivery system can further include a nose cone.

The accessory can be manipulated as a part of the delivery system or independent from the rest of the delivery system. The components of the accessory have the option of being projected outward at the distal end of the delivery system and retracted within. The accessory can undergo rotation in synchrony with the THV to maintain alignment of the THV commissures/sinuses with the accessory. The accessory with its visible components can also undergo translational movement in synchrony or independently from the THV mounted on the delivery system.

Orientation of the accessory components relative to the THV after deployment is maintained to confirm the final THV neo-commissural orientation relative to the native or bioprosthetic valve commissures.

BRIEF DESCRIPTION OF THE DRAWINGS AND FIGURES

FIG. 3A illustrates an exemplary embodiment of an accessory for use with the devices of FIGS. 2A and 2B.

FIG. 3B illustrates another exemplary embodiment of an accessory for use with the devices of FIGS. 2A and 2B.

FIG. 3C illustrates a further exemplary embodiment of an accessory for use with the devices of FIGS. 2A and 2B.

FIG. 3D is a view in partial section of the accessory of FIG. 3A positioned with respect to native or prosthetic valve commissures of a subject in accordance with an exemplary embodiment of the disclosed subject matter.

FIG. 3E is a view in partial section of the accessory of FIG. 3B positioned with respect to native or prosthetic valve commissures of a subject in accordance with an exemplary embodiment of the disclosed subject matter.

FIG. 3F is a view in partial section of the accessory of FIG. 3C positioned with respect to the sinuses of the native or prosthetic valve of a subject in accordance with an exemplary embodiment of the disclosed subject matter.

FIG. 6A is an embodiment of a rotation alignment structure of the device in accordance with an exemplary embodiment of the disclosed subject matter.

FIG. 6B is another embodiment of a rotation alignment structure of the device in accordance with an exemplary embodiment of the disclosed subject matter.

FIG. 6C is a further embodiment of a rotation alignment structure of the device in accordance with an exemplary embodiment of the disclosed subject matter.

DETAILED DESCRIPTION OF THE DISCLOSED SUBJECT MATTER

Figure 1:
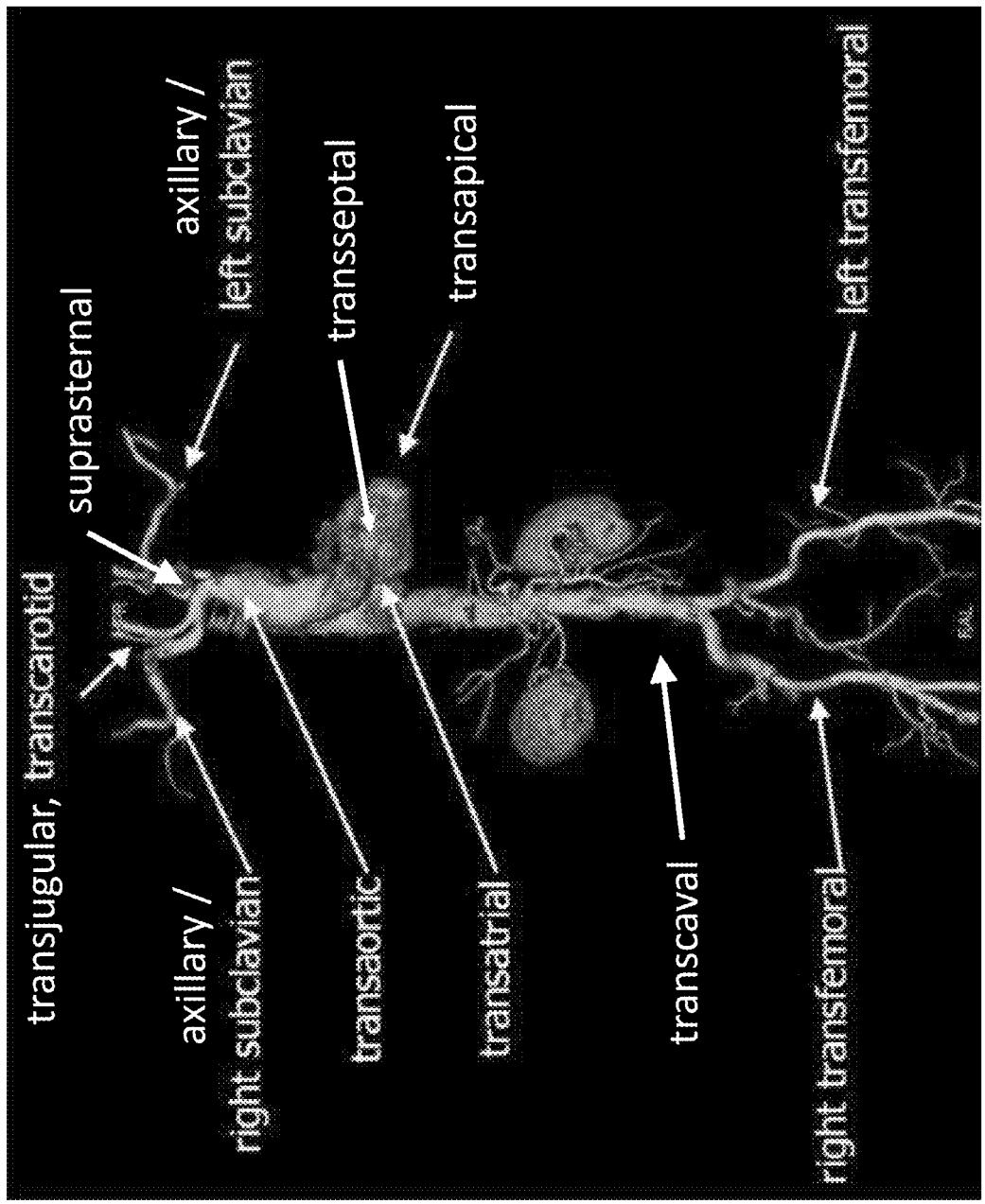
FIG. 1 is a schematic illustrating various transcatheter approaches to deliver a prosthetic heart valve to the heart

While methods, systems and devices are described herein by way of examples and embodiments, those skilled in the art recognize that the methods, systems and devices for delivery and implantation of a prosthetic heart valve in a patient are not limited to the embodiments or drawings described. It should be understood that the drawings and description are not intended to be limited to the particular form disclosed. Rather, the intention is to cover all modifications, equivalents and alternatives falling within the spirit and scope of the appended claims. Any headings used herein are for organizational purposes only and are not meant to limit the scope of the description or the claims. As used herein, the word "may" is used in a permissive sense (i.e., meaning having the potential to) rather than the mandatory sense (i.e., meaning must). Similarly, the words "include," "including," and "includes" mean including, but not limited to.

The basic components of exemplary embodiments of a device for delivery and implantation of a prosthetic heart valve in a patient are described herein. As used in the description, the terms "top," "bottom," "above," "below," "over," "under," "above," "beneath," "on top," "underneath," "up," "down," "upper," "lower," "front," "rear," "back," "forward," "backward" and "left," "right" refer to the objects referenced when in the orientation illustrated in the drawings, which orientation is not necessary for using the devices or achieving the methods described herein. The term "proximal" as used herein is understood to refer to the location further away from the tip of the delivery catheter, proximal to the transcatheter heart valve. The term "distal" as used herein is understood to refer to the location closest to the tip of the delivery catheter.

Aortic

Exemplary embodiments for delivery and implantation of a prosthetic aortic heart valve in a patient are described herein. The delivery system will be either retrograde (trans-femoral, axillary/subclavian, transaortic, transcarotid, transcaval, suprasternal) or antegrade (transapical) (FIG. 1). The design principles of the delivery catheter and accessory are the same but the delivery system lengths will vary based on the approach.

Figure 2A:
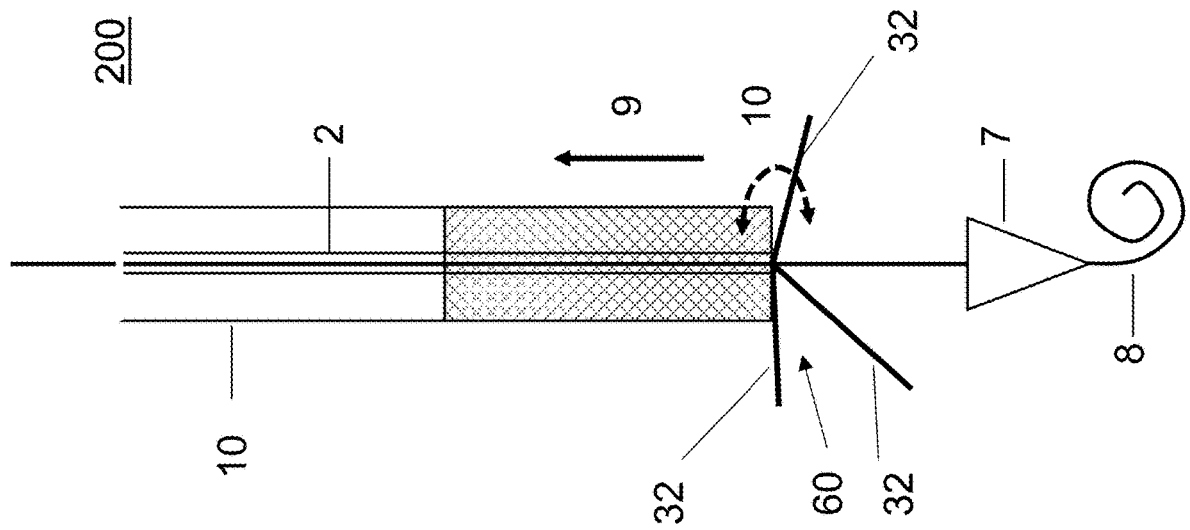
FIG. 2A illustrates an exemplary embodiment of a device configured for delivery and implantation of a prosthetic heart valve in a native or prosthetic heart valve.

An exemplary embodiment of the delivery system 100 is illustrated in FIG. 2A. The system 100 includes the valve delivery catheter 1. As indicated by arrow 3, the delivery catheter 1 has rotational freedom. System 100 further includes accessory 6, delivery shaft 2 for controlling accessory 6, and nose cone 7 for passing over guide wire 8. The accessory 6, advanced to a position distally to the THV 4 near or at the nose cone 7, may include three components, e.g., radially outwardly extending symmetric projections 32.

In some embodiments, projections 32 are fabricated from Nitinol or similar material having elastic and/or shape memory characteristics. During deployment of the THV through the vascular system of the subject, the projections 32 can be compressed within the cone 7 to allow atraumatic passage of the accessory 6 to the valve location. Subsequently, the cone 7 is separately advanced distally to allow the projections 32 to extend to the radially outward configuration of FIG. 2A. In some embodiments, projections 32 can include radiopaque structures or markers to facilitate alignment of the accessory 6, the THV 4 and the subject's anatomy.

Accessory 6 is connected to shaft 2 that is adapted to independently advance, rotate and retract accessory 6 within the delivery catheter 1. The rotational freedom of accessory 6 with respect to delivery catheter 1 is illustrated by arrow 5. An advantage of system 100 is that if the THV 4 needs to be recaptured and repositioned after complete deployment, and if recapturing and repositioning the device may lead to misalignment between the THV commissures and the accessory components, the accessory 6 can be manually rotated to re-align with the THV commissures to confirm orientation relative to native or bioprosthetic valve commissures.

Figure 2B:
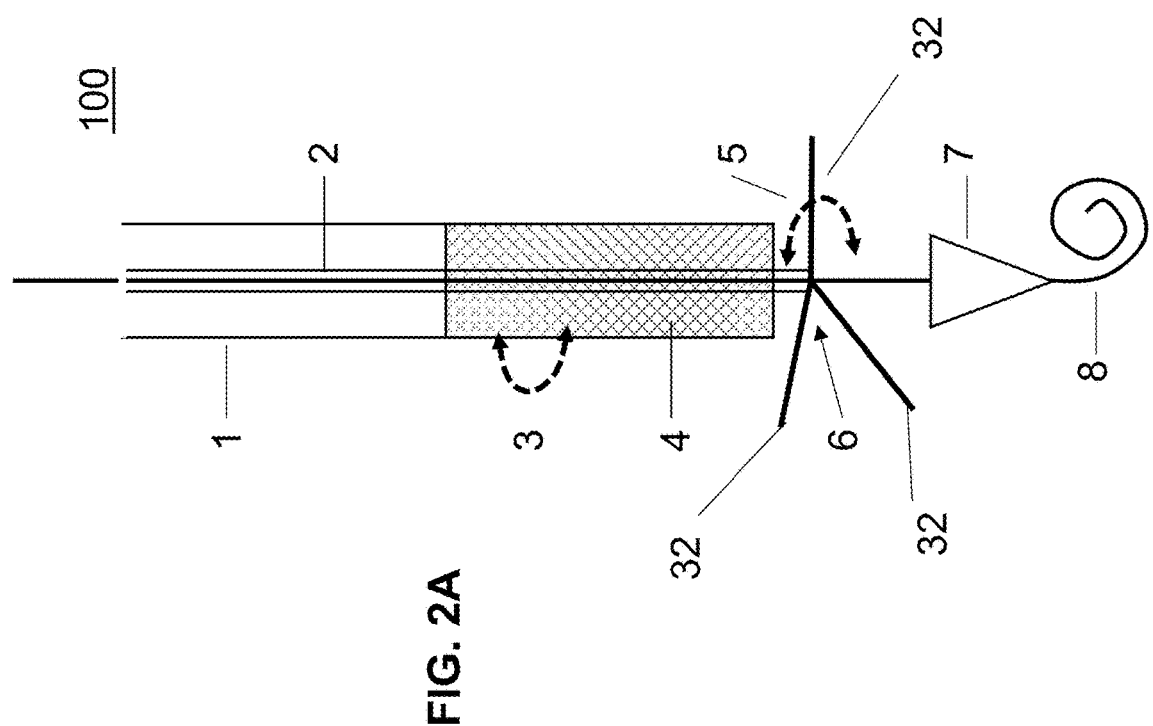
FIG. 2B illustrates another exemplary embodiment of a device configured for delivery and implantation of a prosthetic heart valve in a native or prosthetic heart valve.

Another exemplary embodiment of the system 200 is illustrated in FIG. 2B, and is substantially identical to system 100, with the differences noted herein. The accessory 60 can be an integral part of the valve delivery catheter 10, whereby proximal unsheathing of the THV will expose the accessory 60 distal to the THV and hence the three visible projections 32. System 200 has the benefit of having a simpler delivery catheter 10 having only one movable part (composite valve delivery catheter 10 and accessory 60) instead of two separate independently movable parts.

The components of the accessory can take a variety of shapes and lengths. For example, the accessory can include soft filamentous projections that are atraumatic to the native tissue (accessory 11 illustrated in FIG. 3A and accessory 12 illustrated in FIG. 3B). In the exemplary embodiment shown in FIG. 3A, three components, e.g., projections, are depicted. In the exemplary embodiment of FIG. 3B, accessory 12 includes three components, e.g., three pairs of projections. In some embodiments, the accessory can include "tear-drop"-shaped loops made of soft metallic composites that are flexible and atraumatic (accessory 13 illustrated in FIG. 3C). (While accessory 11, 12 and 13 is illustrated extending from shaft 2 in FIGS. 3A, 3B, 3C, it is understood that the configurations of accessory 11, 12 and 13 are interchangeably used in systems 100 and 200 described herein.)

In some embodiments, the projections are adjustable in length so that they can be extended/retracted as desired (not shown). In the exemplary embodiments shown in FIGS. 3A, 3B and 3C, each projection is capable of being moved independently. Furthermore, each projection can exhibit a variable radius of curvature such that the projections can be articulated (or "curled") to conform to a desired valve contour.

As illustrated in FIG. 3D, accessory 11 (illustrated in FIG. 3A) can be positioned to align with native or prosthetic valve commissures C. As illustrated in FIG. 3E, accessory 12 (illustrated in FIG. 3B) can be positioned to straddle between each commissure C of the native or bioprosthetic aortic valve to aid in alignment with the THV commissure. As illustrated in FIG. 3F, accessory 13 (illustrated in FIG. 3C) can be positioned above the sinuses of the native or prosthetic valve in alignment with the valve leaflets L.

The accessory components can include radiopaque parts to aid in accurate visualization under fluoroscopy, and also include echogenic parts to aid in visualization under echocardiography. However, the accessory components will not have parts that would visually or mechanically interfere with visualization and accuracy of the THV deployment under fluoroscopy or echocardiography.

Figure 4B:
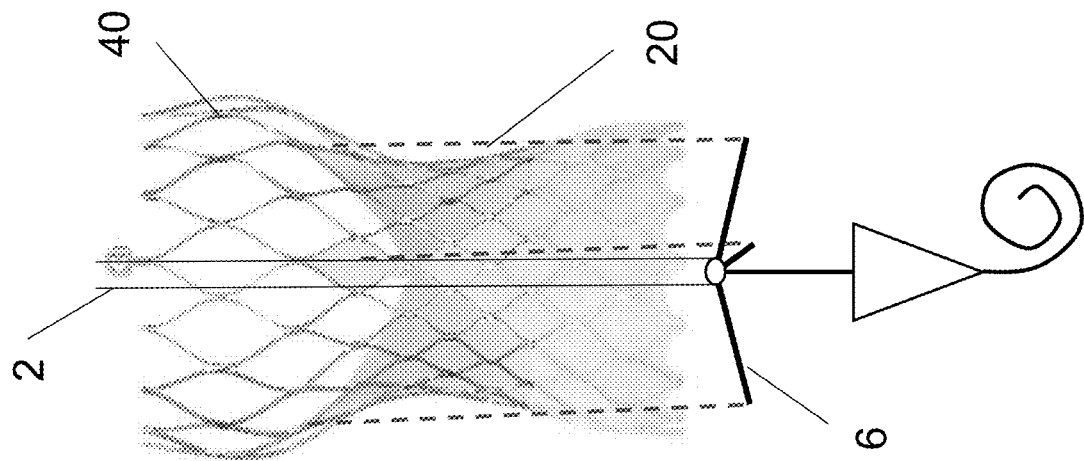
FIG. 4B is side view of the device of FIGS. 2A and/or 2B with portions of the accessory in substantial alignment with the commissural posts of the self-expanding or mechanically-expanding THV in accordance with an exemplary embodiment of the disclosed subject matter.
Figure 4A:
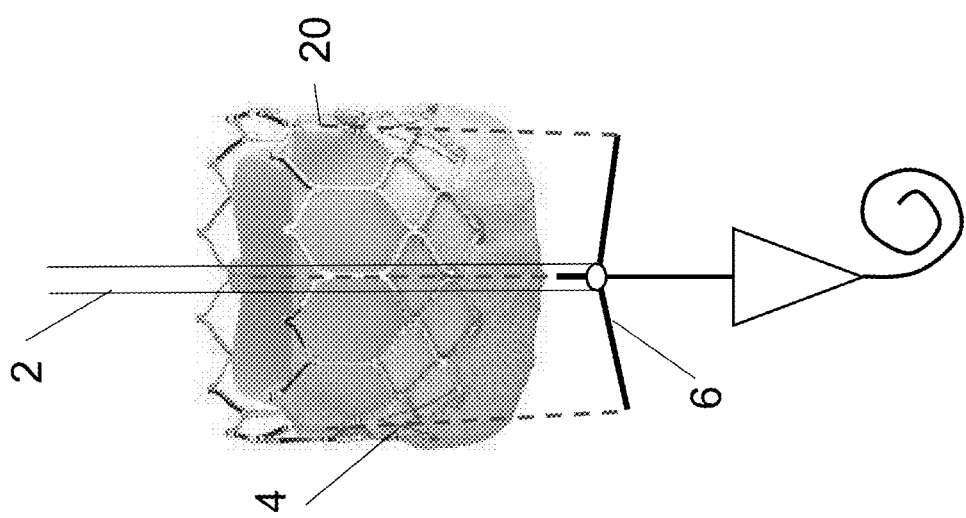
FIG. 4A is side view of the device of FIGS. 2A and/or 2B with portions of the accessory in substantial alignment with the commissural posts of the balloon expandable THV in accordance with an exemplary embodiment of the disclosed subject matter.

During the surgical procedure, the projections of the accessory 6 will be either in a first "aligned" configuration, e.g., aligned with the commissural posts 20 (illustrated with dotted lines) of the THV (illustrated in FIG. 4A with balloon expanding transcatheter heart valve 4 and FIG. 4B with self-expanding or mechanically-expanding transcatheter heart valve 40), or alternatively, in a second "offset" configuration, e.g., offset by, e.g., 60 degrees (illustrated in FIG. 4C with balloon expanding transcatheter heart valve 4 and FIG. 4D with self-expanding or mechanically-expanding transcatheter heart valve 40), at the base of sinus of transcatheter heart valve between two commissural posts 20 (illustrated with dotted lines), prior to mounting and crimping onto the delivery catheter such that during valve delivery and deployment the alignment will be maintained.

Figure 5B:
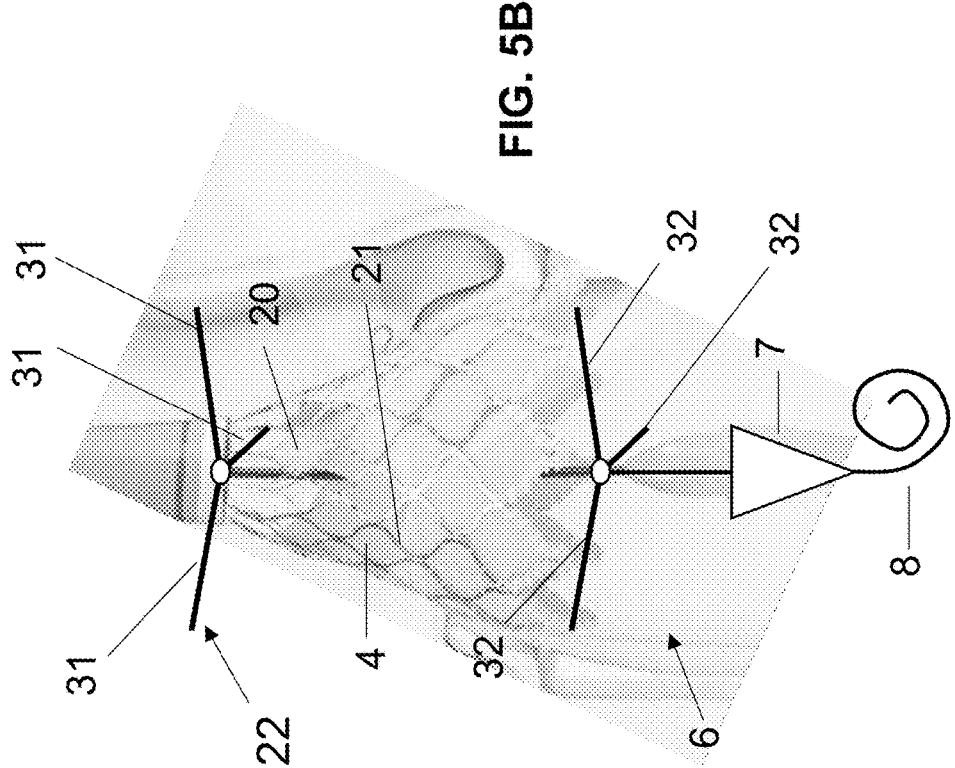
FIG. 5B illustrates the embodiment of FIG. 5A with the THV partially deployed in accordance with an exemplary embodiment of the disclosed subject matter.
Figure 5A:
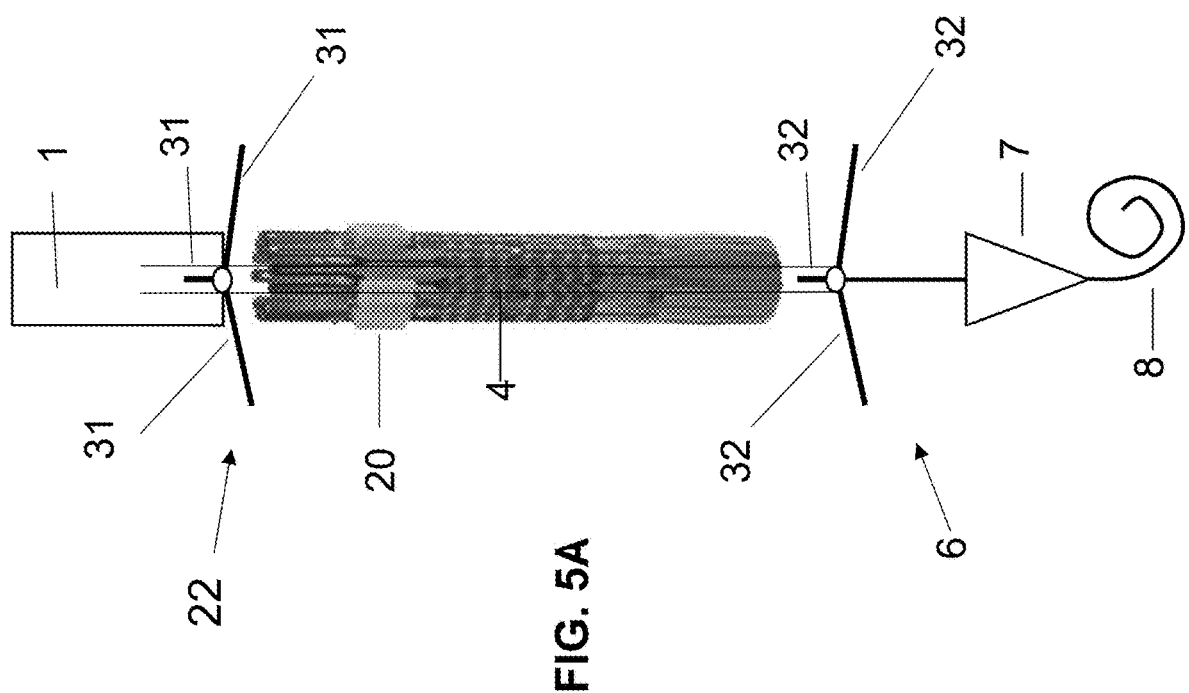
FIG. 5A illustrates a further embodiment of the device of FIG. 2A.

In some embodiments, the accessory 6 includes both a distal portion including distal projections 32 and a proximal portion 22 including proximal projections 31, such that after the THV 4 is positioned or deployed, the portion 22 of accessory 6 located proximal to the THV can be used to confirm orientation (FIG. 5A-5B). The base of the sinus of the transcatheter heart valve 21 is illustrated in FIG. 5B.

Figure 4D:
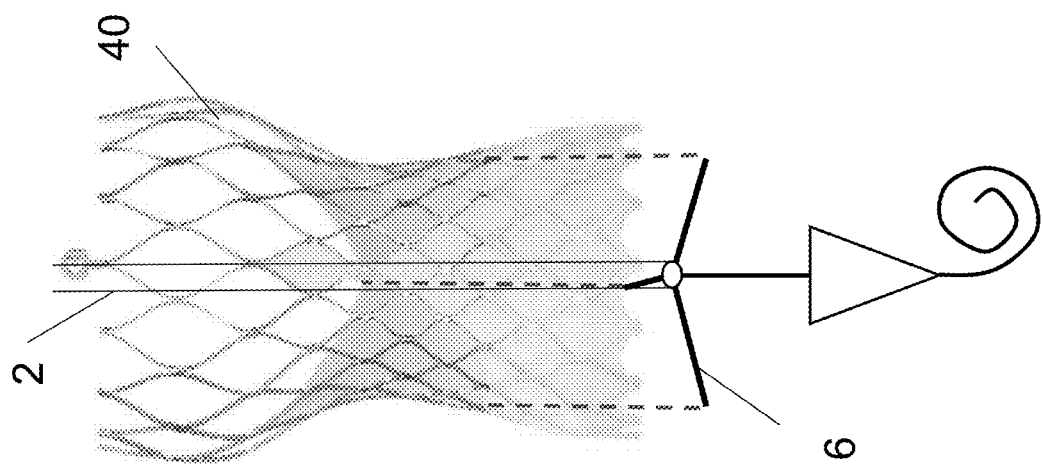
FIG. 4D is side view of the device of FIGS. 2A and/or 2B with portions of the accessory substantially offset from the commissural posts of the self-expanding or mechanically-expanding THV in accordance with an exemplary embodiment of the disclosed subject matter.
Figure 4C:
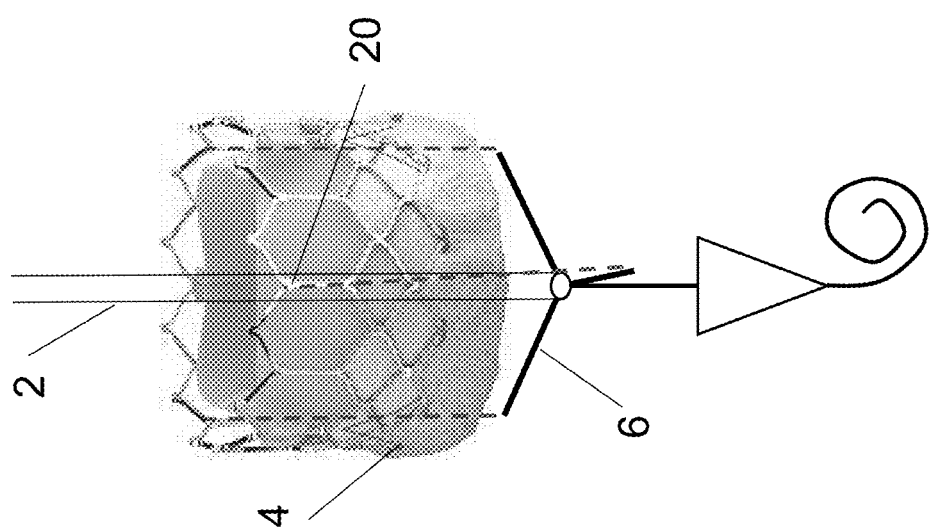
FIG. 4C is side view of the device of FIGS. 2A and/or 2B with portions of the accessory substantially offset from the commissural posts of the balloon expandable THV in accordance with an exemplary embodiment of the disclosed subject matter.

In some embodiments, e.g., system 100 (FIG. 2A), the valve delivery catheter 1 and the accessory 6, which can be independently manipulated, further include a locking and unlocking mechanism such that both parts can be locked together to maintain alignment between the accessory components and the THV commissures 20 in both "aligned" configuration (FIGS. 4A-4B) and "offset" configuration (FIGS. 4C-4D). In some embodiments, the locking mechanism is located within the handle/housing 26 (not shown).

In some embodiments, e.g., system 100 (FIG. 2B), because the valve delivery catheter 10 and the accessory 60 are a single unit, the THV commissures and the accessory components would be aligned at all times.

Alignment accessory control is provided. The delivery catheter 1 can include an independent mechanism to rotate the THV 4 and accessory 6 in unison to maintain the alignment between the components on the accessory and the THV commissures 20 to optimize the alignment between THV commissures 20 to the native or bioprosthetic aortic valve commissures, prior to valve implantation. This mechanism can include a turning wheel or knob 25 on the delivery system handle 26, such that one-to-one rotational alignment between the turning wheel 25 and the accessory 6 (not shown) is possible to allow accurate orientation of the THV relative to the native or bioprosthetic valve commissures or sinuses (FIG. 6A). FIG. 6B illustrates another embodiment of the knob 27 on system handle 26. Dotted arrows on FIGS. 6A and 6B illustrate rotation movement of knobs 25, 27, respectively. FIG. 6C illustrates another embodiment including a translational slide 28 operative with a helical screw or other similar configuration on system handle 26 to provide rotational alignment of the THV relative to the native or bioprosthetic valve commissures or sinuses. Solid arrows on FIG. 6C illustrate translation movement of slide 28.

The manual rotational alignment between the THV 4 and the native or bioprosthetic aortic valve commissures can occur prior to THV positioning across the native aortic annulus or bioprosthetic aortic valve, or after the THV 4 is fully deployed if the THV can be repositioned or recaptured.

Figure 7B:
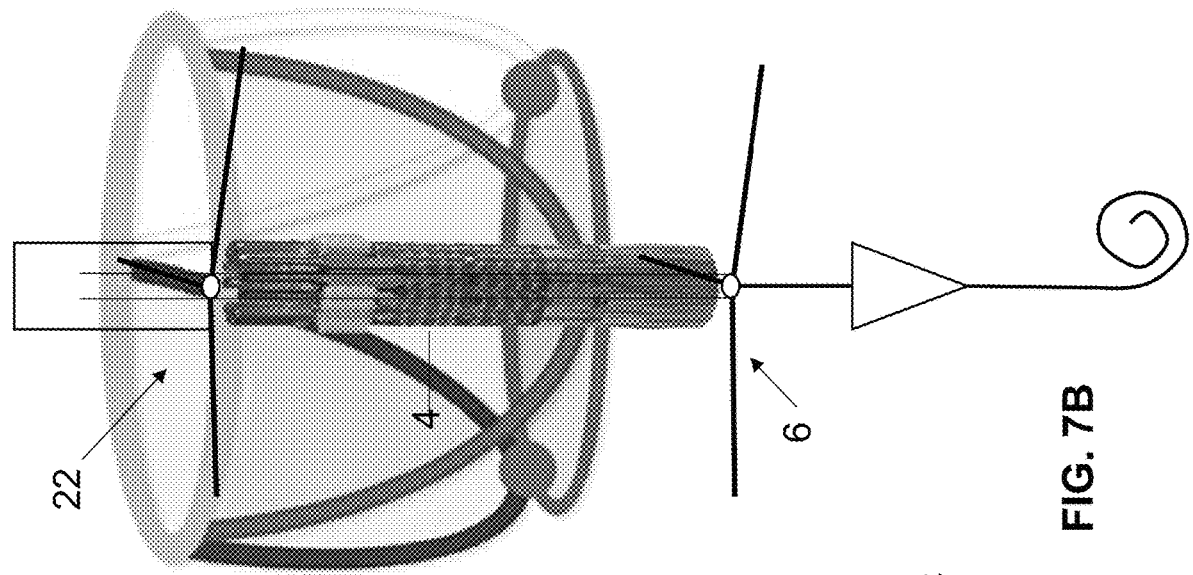
FIG. 7B illustrates the device of FIG. 6A prior to deployment of the THV, such that the component is positioned through the aortic valve annulus.
Figure 7A:
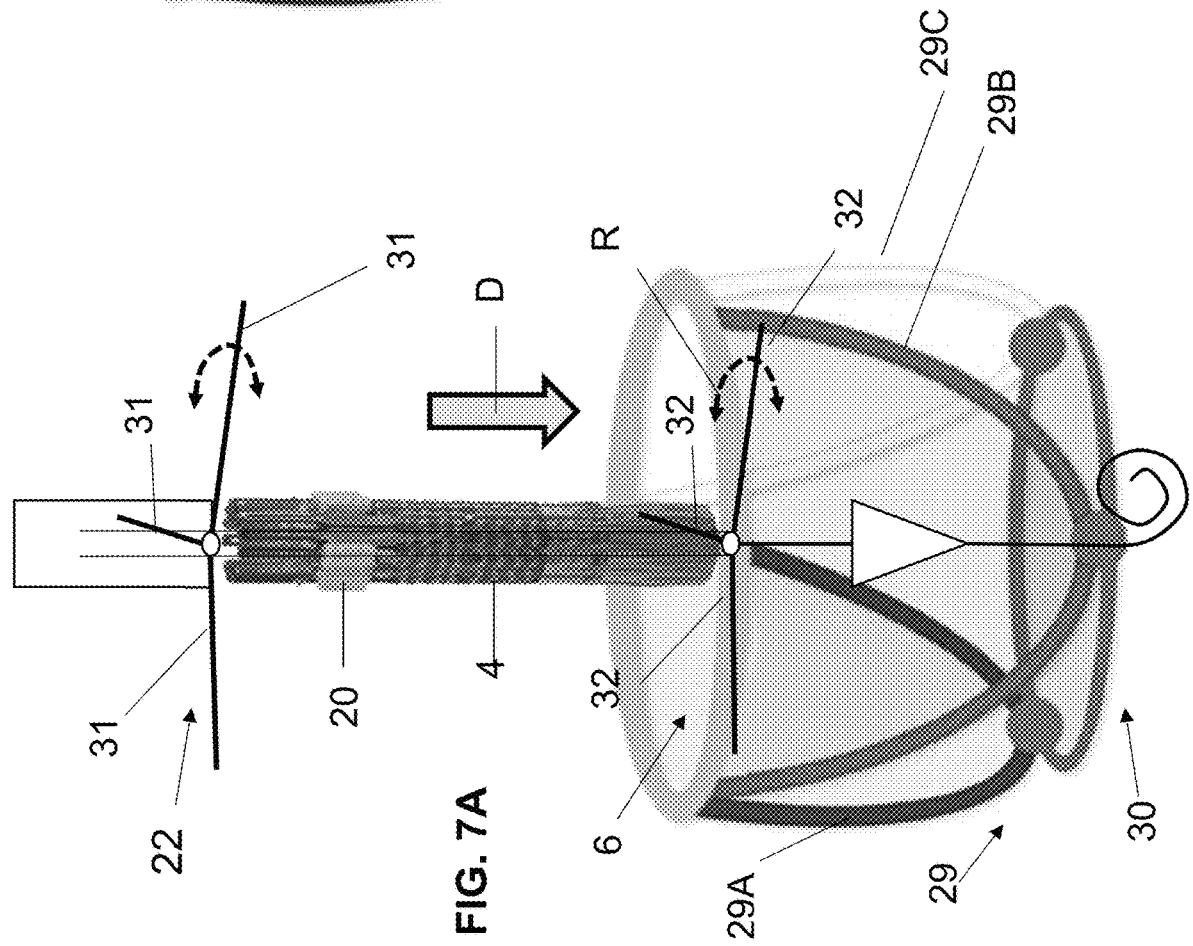
FIG. 7A illustrates the device of FIG. 6A prior to deployment of the THV positioned at the aortic root above the aortic valve annulus.

FIG. 7A illustrates the balloon-expandable transcatheter heart valve 4 crimped prior to deployment. The accessory 6 is positioned at the aortic root 29 (including sinuses 29A, 29B, 29C) above the aortic valve annulus 30, such the projections 32 of accessory 6 are aligned with the native aortic valve commissures. The dashed line R illustrates rotational alignment of the transcatheter heart valve 4 with the commissures. Proximal portion 22 of the accessory 6 includes corresponding outwardly extending projections 31. Arrow D illustrates the direction of distal advancement of the transcatheter heart valve 4 and the accessory 6 across the annulus 30, resulting in the position of the transcatheter heart valve 4 and accessory 6 illustrated in FIG. 7B.

Figure 8B:
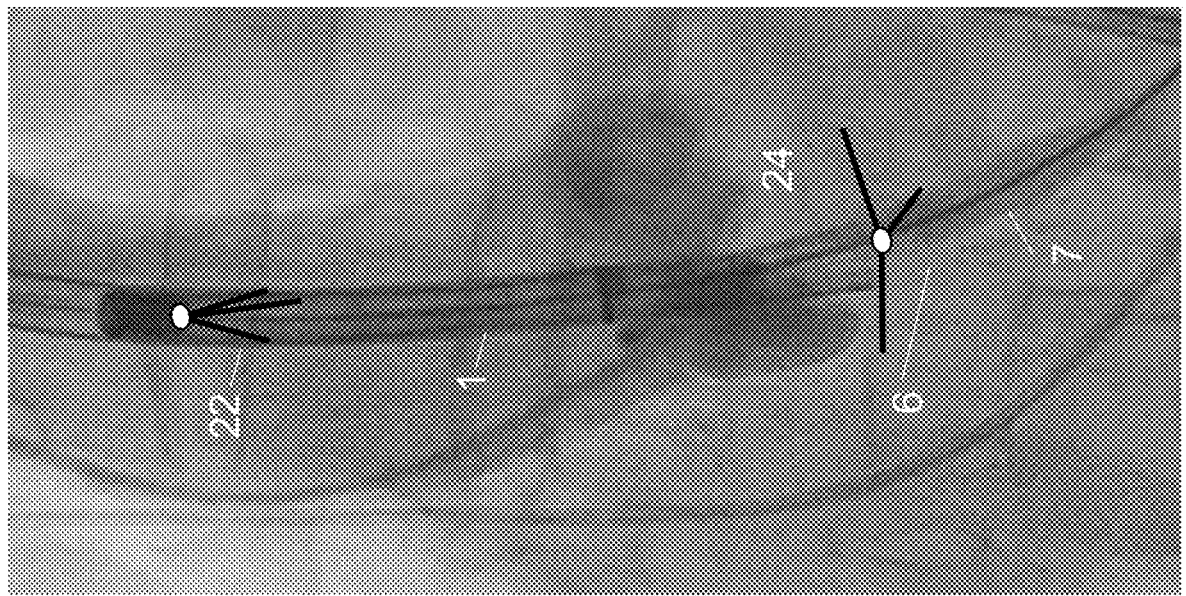
FIG. 8B is a fluoroscopic view of the procedure of FIG. 8A in accordance with an exemplary embodiment of the disclosed subject matter.
Figure 8A:
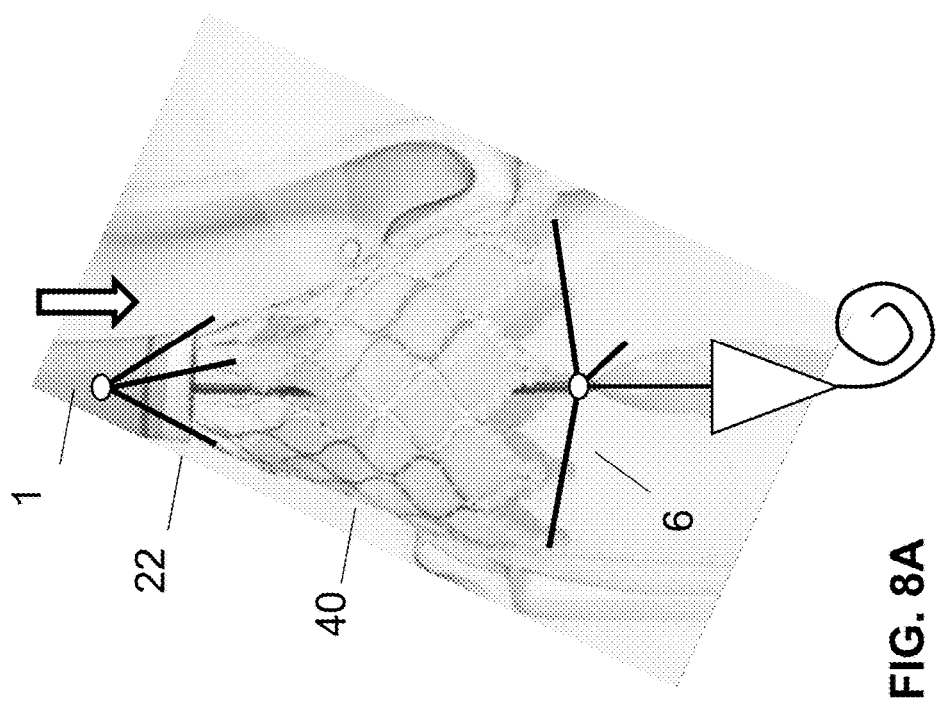
FIG. 8A illustrates re-collapse of a portion of the accessory of the device to assist in repositioning of the THV in accordance with an exemplary embodiment of the disclosed subject matter.

The case where the THV 4 would need to be partly or fully recaptured before rotational alignment can be performed, e.g., to avoid interaction with the native or bioprosthetic aortic valve, is illustrated in FIGS. 8A-8B. As illustrated in FIG. 8A, arrow R represents distal movement of the valve delivery catheter 1 recapturing a self-expanding/mechanically-expanding transcatheter heart valve 40 which will recollapse the proximal components 22 of the accessory 6 within the catheter 1, resulting in the fluoroscopic view illustrated in FIG. 8B.

Additionally or alternatively, the alignment accessory control 2 can adjust the pitch and/or yaw of the THV 4/40 and/or accessory 6 to orient the components to conform to the native commissures. In some embodiments, the THV 4/40 and/or accessory 6 can be rotated up to 360 degrees; the pitch and yaw (measured relative to a longitudinal central axis of the THV) can be adjusted by up to 90 degrees.

In situations where the accessory components may straddle between each aortic valve commissure or to the base of the aortic sinus after THV deployment, the relative rotational misalignment between the accessory components and THV commissures can be visualized and identified by rotational fluoroscopy. In this case, the THV can be recaptured and repositioned for improved alignment with the native or bioprosthetic valve commissures, as visualized by the accessory components.

Figure 9:
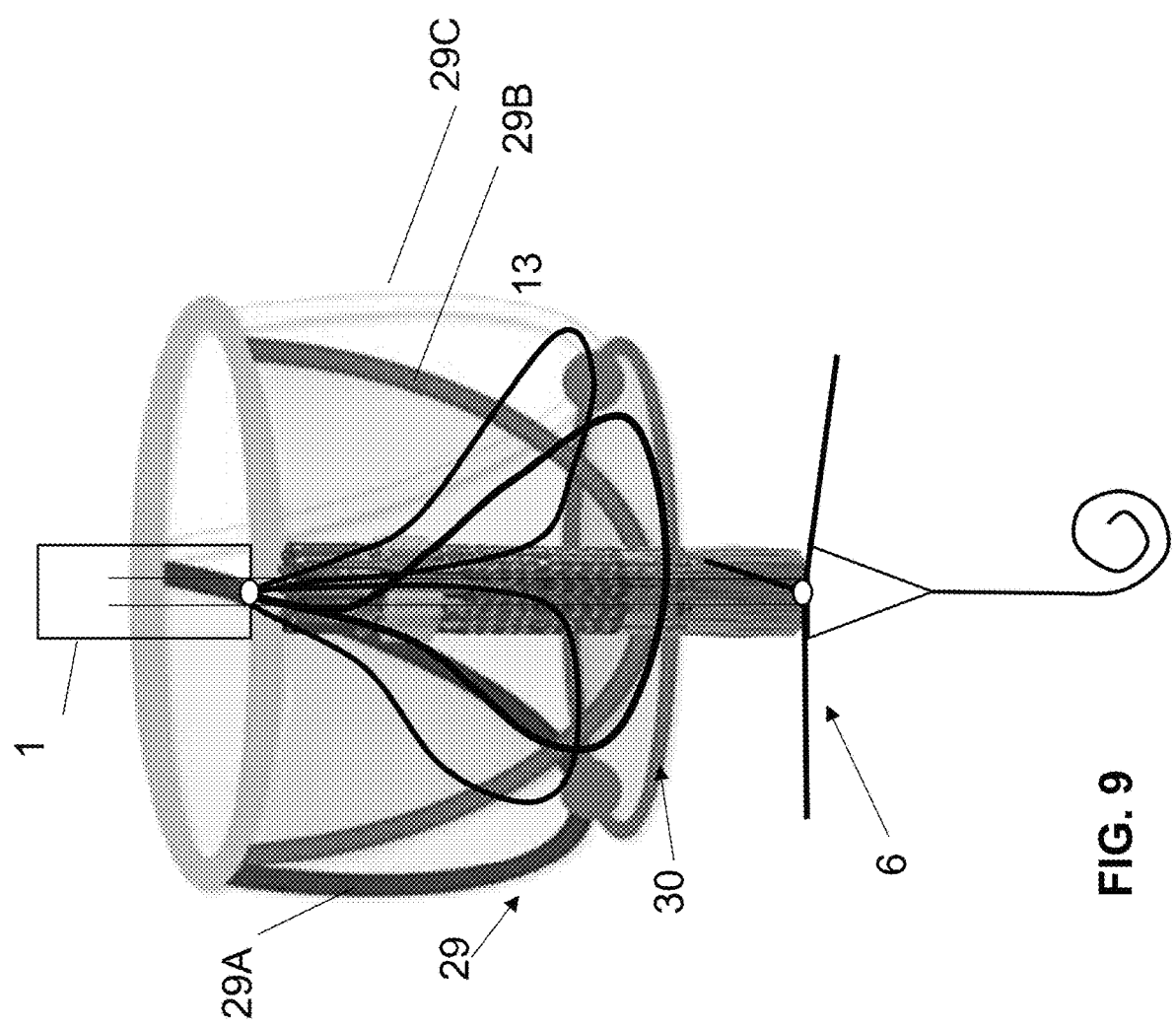
FIG. 9 illustrates the positioning of the device in accordance with an exemplary embodiment of the disclosed subject matter.

In balloon-expandable THV 4, the projections 32 of the accessory 6 may be loaded through the top row of open cells of the THV frame, such that the projections 32 will be positioned equidistant (60 degrees) from the three commissural posts. The projections 32 will be extended to position at the base of the three aortic sinuses 29A, 29B, 29C during THV positioning and deployment. FIG. 9 showing it can be mounted across the open cells of a balloon expandable transcatheter heart valve such that each component will be oriented and positioned above the base of the sinus prior to valve deployment.

After THV is deployed, these components of the accessory can be withdrawn and retrieved via the THV delivery system through an independent mechanism.

Figure 10B:
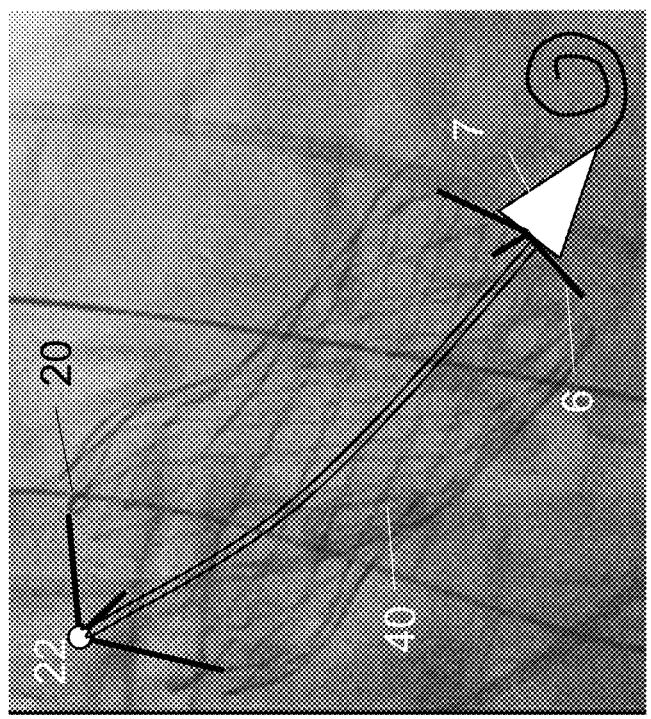
FIG. 10B is a fluoroscopic view illustrating the orientation of the accessory after deployment of a self-expandable THV.
Figure 10A:
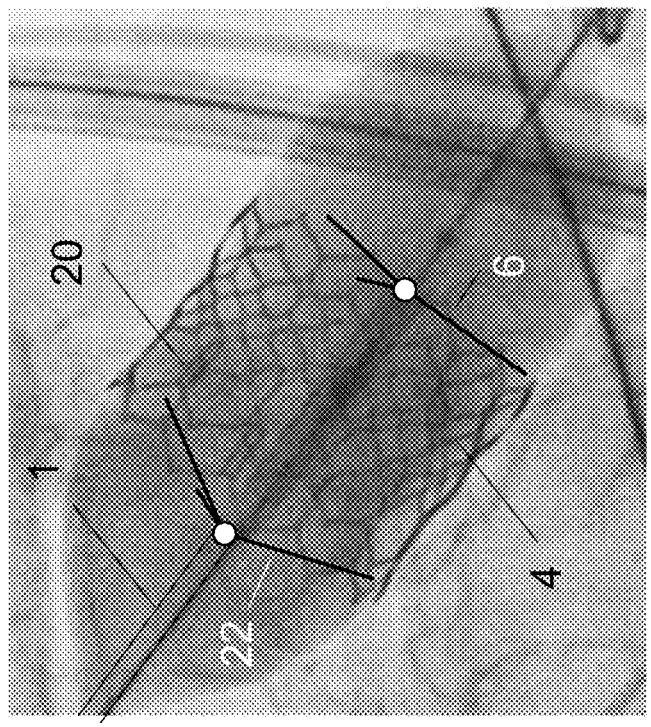
FIG. 10A is a fluoroscopic view illustrating the orientation of the accessory after deployment of a balloon-expandable THV.

After the THV is deployed, the positions of the accessory components relative to the THV commissures identified on fluoroscopy determine the final THV orientation relative to the native or bioprosthetic aortic valve commissures. FIG. 10A illustrates the orientation of the accessory 6 after deployment of balloon-expandable transcatheter heart valve 4. FIG. 10B illustrates the orientation of the accessory 6 after deployment of self-expanding transcatheter heart valve 40.

The accessory components in system 100 may be manipulated and retracted after the THV is deployed. In system 200, after the valve delivery catheter is withdrawn from the THV, the accessory components can be resheathed over by the delivery catheter capsule to avoid interference with native issue to allow safe removal of the valve delivery system.

A cerebral embolic protection system may be mounted to the accessory to reduce stroke risk. In this version, the accessory components will span the diameter of the ascending aorta such that the cerebral embolic protection system can be fully deployed. In this version, only the accessory containing the cerebral embolic protection system will operate independently from the valve delivery catheter (similar to the interaction of catheter 1 and accessory 6 of system 100 described herein).

Mitral

Exemplary embodiments for delivery and implantation of a prosthetic mitral heart valve in a patient are described herein. The delivery system can be either an antegrade (transseptal, transatrial) or retrograde (transapical) approach to the mitral valve (FIG. 1). The design principles of the delivery catheter and accessory are the substantially identical to the systems 100 and 200 described herein above; however, the delivery system lengths will vary based on the approach.

According to a first mitral embodiment (substantially identical to system 100), the accessory 6, located distal (+/− proximal) to the THV, includes at least three symmetric projections 32 that include radiopaque structures and a shaft to independently advance, rotate and retract within the delivery system. An advantage of this design is that if the THV needs to be recaptured and repositioned after complete deployment, and if recapturing and repositioning the device may lead to misalignment between the THV commissures and the accessory components, the accessory can be manually rotated to re-align with the THV commissures to confirm orientation relative to native or bioprosthetic valve commissures.

According to a second mitral embodiment (substantially identical to system 200), the accessory 60, located distal (+/− proximal) to the THV, can be an integral part of the valve delivery catheter 10, whereby proximal unsheathing of the THV during deployment will expose the accessory 60 distal to the THV and hence at least the three visible projections 32. This concept has a benefit of having a simpler delivery catheter with only one movable part (composite valve delivery catheter and accessory) instead of two separate independently movable parts.

As with the aortic accessory, the accessory components for the mitral application can take a variety of shapes, including soft and flexible filamentous projections that are atraumatic to the native tissue. The accessory components may be positioned to align with the commissures of the native mitral valve, center of posterior annulus, or bioprosthetic valve commissures, in addition to alignment with the THV commissures. The accessory components can include radiopaque parts to aid in accurate visualization under fluoroscopy, and also can include echogenic parts to aid in visualization under echocardiography. However, the accessory components will not have parts that would visually or mechanically interfere with visualization and accuracy of the THV deployment under fluoroscopy or echocardiography.

The components on the accessory will be aligned with the commissural posts of the THV prior to mounting and crimping onto the delivery catheter such that during valve delivery and deployment the alignment will be maintained. In the first mitral embodiment, the valve delivery catheter and the accessory, which can be independently manipulated, include a locking and unlocking mechanism such that both parts can be locked together to maintain alignment between the accessory components and the THV commissures. In the second mitral embodiment, because the valve delivery catheter and the accessory for a single unit, the THV commissures and the accessory components would be aligned at all times.

Figure 11:
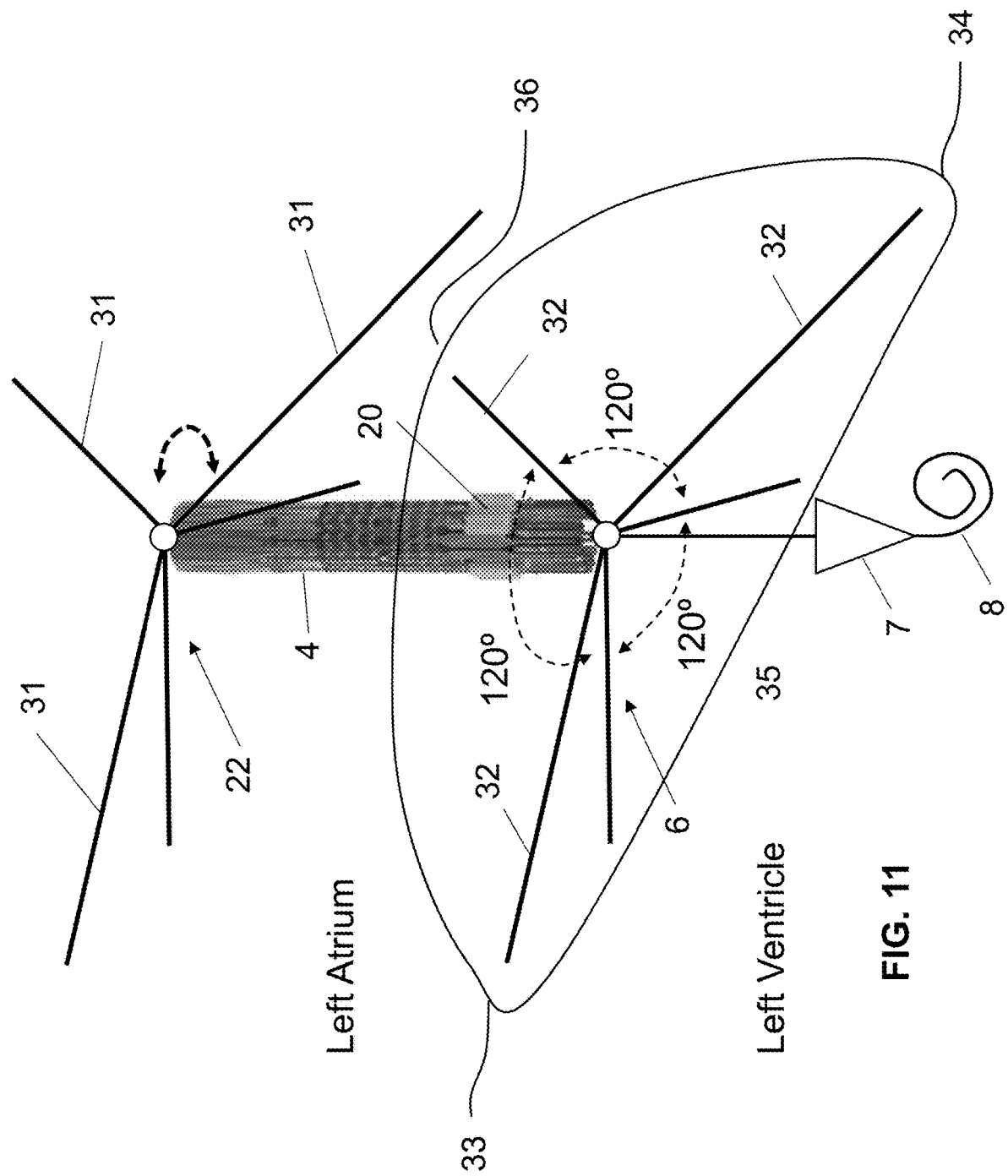
FIG. 11 illustrates the positioning of the device with respect to the medial commissure, the lateral commissure, the anterior annulus, and the posterior annulus of the mitral valve.

FIG. 11 illustrates the positioning of the system 100 with respect to the medial commissure 33, the lateral commissure 34, the anterior annulus 35, and the posterior annulus 36 of the mitral valve. Accessory 6 includes projections 32 located distal to the transcatheter heart valve 4, to be oriented to the medial and lateral commissures, and the distal portion of the accessory 22 includes projections 31 located proximal to the transcatheter heart valve 4, to be oriented to the medial and lateral commissures. The projections 31 and 32 are oriented 120 degrees apart from each other to aid in alignment of transcatheter heart valves with prosthetic heart valves. In some embodiments, one projection of the accessory 6 will always face the middle of the posterior mitral valve annulus 36.

Figure 12:
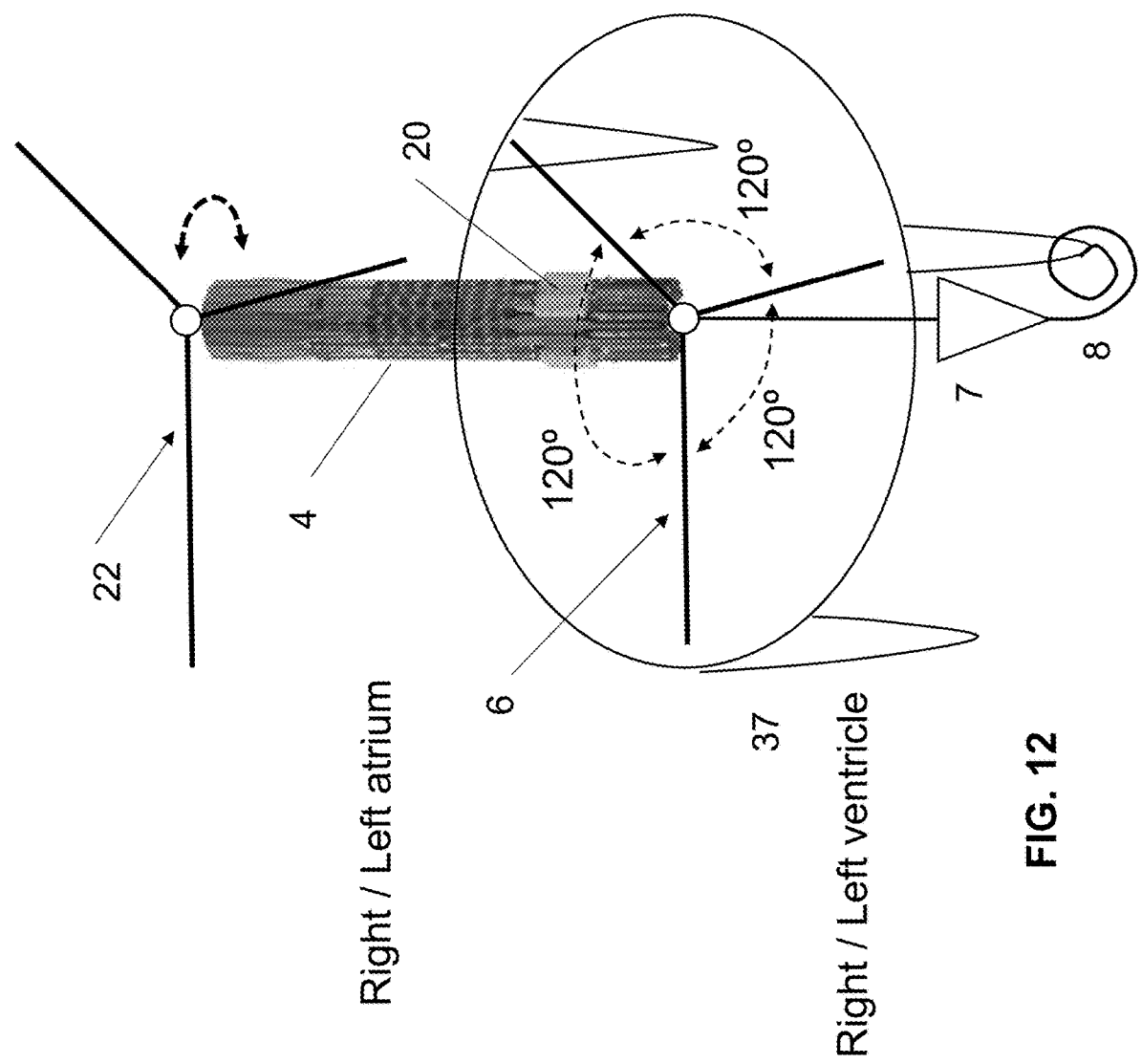
FIG. 12 illustrates the orientation of the THV and the accessory of FIG. 5A to align with the commissures of the prosthetic heart valve.

FIG. 12 illustrates the orientation of the transcatheter heart valve 4 in its crimped form, aided by the projections 31, 32 to align with the commissures 20 of the prosthetic heart valve 37.

The delivery catheter includes an independent mechanism to rotate the THV and accessory in unison to maintain the alignment between the components on the accessory and the THV commissures to optimize the alignment between THV commissures to the native mitral valve commissures and the center of posterior mitral annulus, or bioprosthetic mitral valve commissural posts, prior to THV implantation. In some embodiments, this mechanism is a turning wheel or knob on the delivery system handle, such that one-to-one rotational alignment between the turning wheel and the accessory is possible to allow accurate orientation of the THV relative to the native commissures and center of the posterior annulus or bioprosthetic mitral valve commissures. (See, e.g., FIGS. 6A-6C).

Figure 13B:
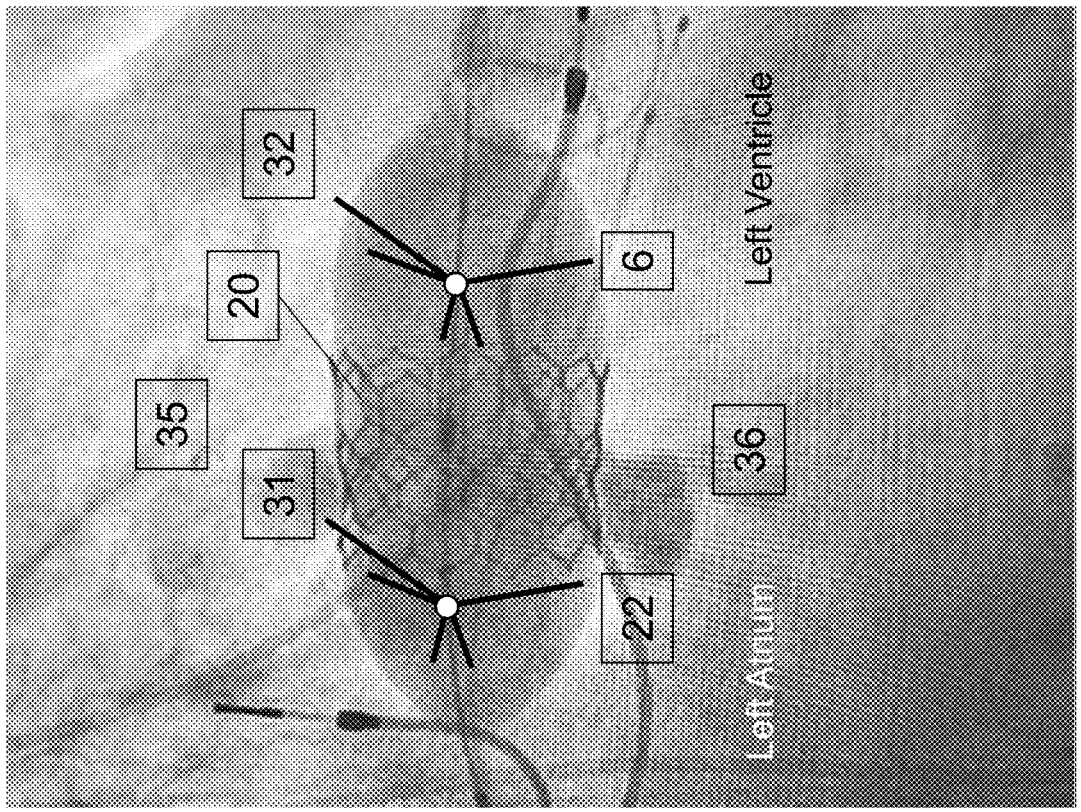
FIG. 13B is a fluoroscopic visualization of the accessory after transcatheter heart valve deployment in transcatheter mitral valve replacement in native mitral valve.
Figure 13A:
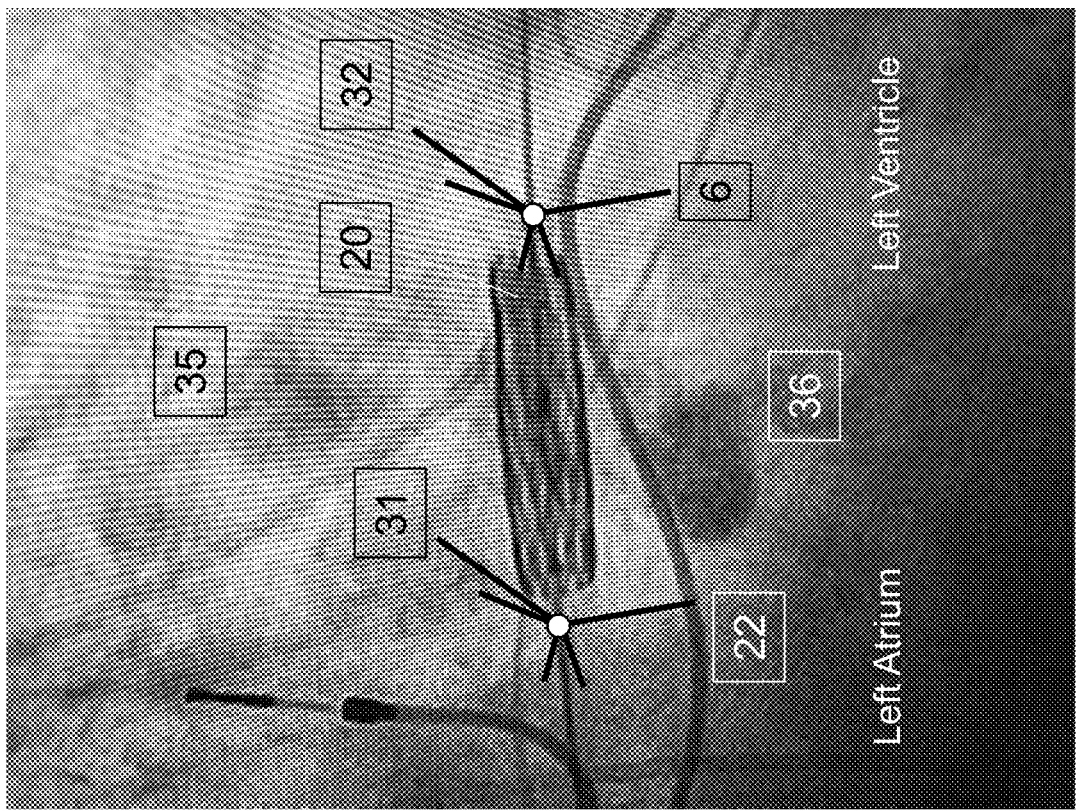
FIG. 13A is a fluoroscopic visualization of the accessory during transcatheter heart valve positioning in native mitral valve.
Figure 14A:
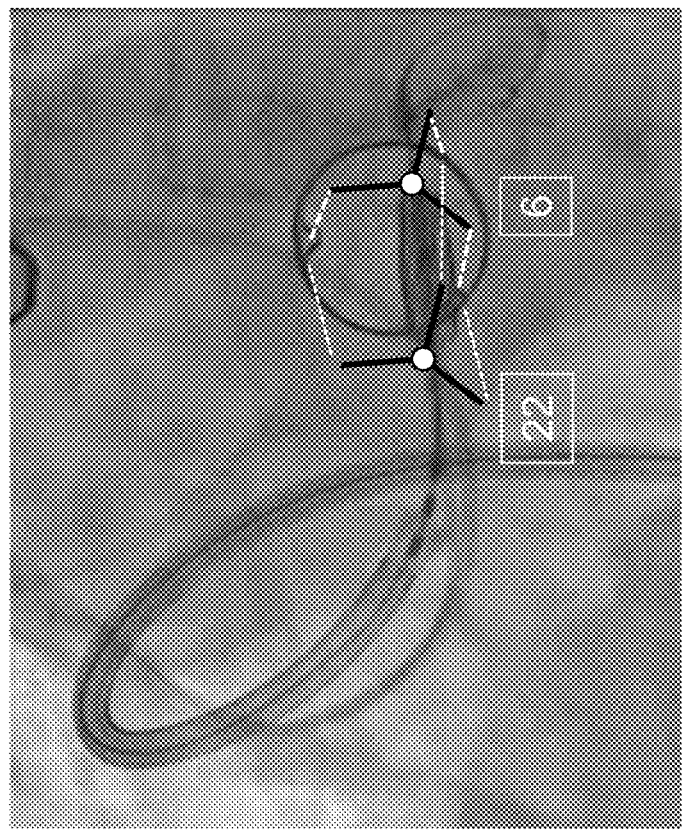
FIG. 14A is a fluoroscopic visualization of the accessory during transcatheter heart valve positioning in a prosthetic mitral valve.

The manual rotational alignment between the THV and the native or bioprosthetic mitral valve commissures can occur prior to or during THV positioning across the native mitral annulus or bioprosthetic mitral valve, or after the THV is fully deployed if the THV can be repositioned or recaptured (FIGS. 13A, 14A). In the latter case, the THV would need to be partly or fully recaptured before rotational alignment can be performed to avoid THV interacting with the native or bioprosthetic mitral valve.

In situations where the accessory components face the native mitral commissures and center of posterior annulus, or the bioprosthetic mitral commissures, after THV deployment, the relative rotational misalignment between the accessory components and THV commissures can be visualized and identified. In this case, the THV can be recaptured and repositioned for improved alignment relative to the commissures, as visualized by the accessory components.

Figure 14B:
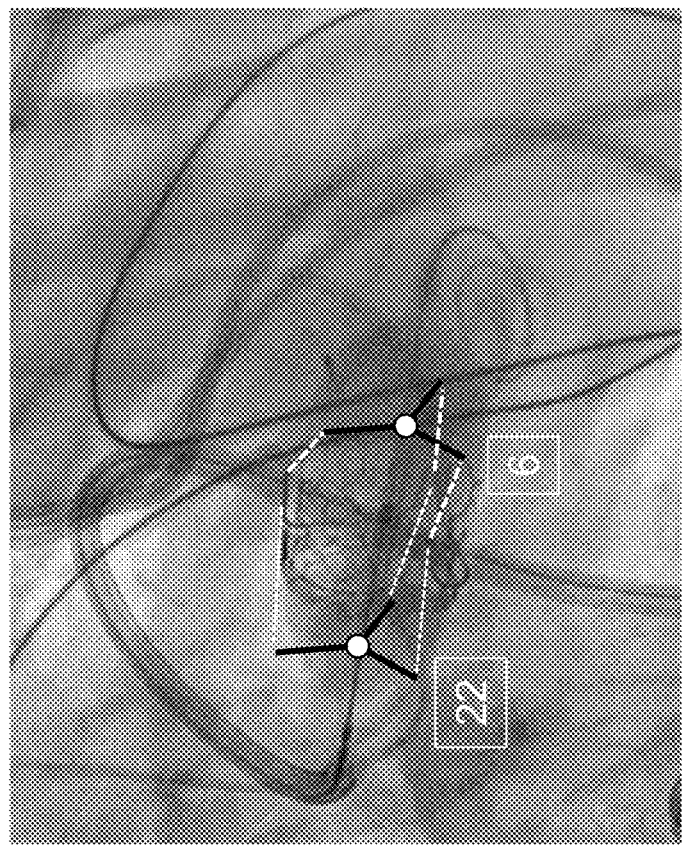
FIG. 14B is a fluoroscopic visualization of the accessory after transcatheter heart valve deployment in transcatheter mitral valve replacement in a prosthetic mitral valve.

After the THV is deployed, the positions of the accessory components relative to the THV commissures identified on fluoroscopy determine the final THV orientation relative to the native or bioprosthetic mitral valve commissures (FIG. 13B, 14B).

The accessory components in system 100 may be manipulated and retracted after the THV is deployed. In system 200, after the valve delivery catheter is withdrawn from the THV, the accessory components can be resheathed over by the delivery catheter capsule to avoid interference with native issue to allow safe removal of the valve delivery system.

Tricuspid

Exemplary embodiments for delivery and implantation of a prosthetic tricuspid heart valve in a patient are described herein. The delivery system will be an antegrade (transfemoral, transjugular, transaxillary) approach to the tricuspid valve (FIG. 1). The design principles of the delivery catheter and accessory are the same as for the mitral valve but the accessory will consist of components based on the anatomy of the native or bioprosthetic tricuspid valve.

Having described and illustrated the principles of our invention with reference to the described embodiments, it will be recognized that the described embodiments can be modified in arrangement and detail without departing from such principles. It should be understood that the systems, processes, or methods described herein are not related or limited to any particular type of environment, unless indicated otherwise.

In view of the many possible embodiments to which the principles of our invention can be applied, we claim as our invention all such embodiments as can come within the scope and spirit of the following claims and equivalents thereto.

What is claimed is:

1. A medical device for delivery of a transcatheter heart valve (THV) to a subject, the device comprising:
   an elongated member;
   a THV;
   an accessory for receiving the THV thereon and extending from a distal portion of the elongated member, the accessory comprising a plurality of radially outwardly extending projections configured and spaced to align with a leaflet or a commissure of a native or bioprosthetic valve and disposed distally and spaced apart from the THV during delivery of the THV for alignment of the THV with respect to a native or bioprosthetic valve commissure or a valve leaflet at a desired angle during delivery of the THV and wherein the radially outwardly extending projections are spaced apart from the THV,
   the medical device further comprising projections disposed at a proximal portion of the THV during delivery of the THV, and
   a rotational member connected to the elongated member to rotate the accessory and THV together to align with the native or bioprosthetic valve commissure or the valve leaflet at a desired angle.

2. The medical device of claim 1, further comprising a delivery catheter housing the THV therein, wherein the delivery catheter and the accessory are independently rotatable.

3. The medical device of claim 1, wherein the projections extend radially outwardly from the elongated member.

4. The medical device of claim 1, wherein each projection is capable of being moved independently.

5. The medical device of claim 1, wherein the elongated member and the THV are adapted for deployment to the aortic valve of the subject, the mitral valve of the subject, or the tricuspid valve of the subject.

6. The medical device of claim 1, wherein the projections are capable of being compressed within a delivery catheter during delivery.

7. The medical device of claim 1, further comprising a nose cone positioned distal of the accessory.

8. A medical device for delivery of a transcatheter heart valve (THV) to a subject, the device comprising:
an elongated member;
a THV
an accessory for receiving the THV thereon and extending from a distal portion of the elongated member, the accessory comprising a plurality of radially outwardly extending projections configured and spaced to align with a leaflet or a commissure of a native or bioprosthetic valve and disposed distally and spaced apart from the THV during delivery of the THV for alignment of the THV with respect to a native or bioprosthetic valve commissure or a valve leaflet at a desired angle during delivery of the THV and wherein the radially outwardly extending projections are spaced apart from the THV, and
a rotational member connected to the elongated member to rotate the accessory and THV together to align with the native or bioprosthetic valve commissure or the valve leaflet at a desired angle,
wherein the projections are atraumatic filamentous projections.

9. A medical device for delivery of a transcatheter heart valve (THV) to a subject, the device comprising:
an elongated member;
a THV
an accessory for receiving the THV thereon and extending from a distal portion of the elongated member, the accessory comprising a plurality of radially outwardly extending projections configured and spaced to align with a leaflet or a commissure of a native or bioprosthetic valve and disposed distally and spaced apart from the THV during delivery of the THV for alignment of the THV with respect to a native or bioprosthetic valve commissure or a valve leaflet at a desired angle during delivery of the THV and wherein the radially outwardly extending projections are spaced apart from the THV, and
a rotational member connected to the elongated member to rotate the accessory and THV together to align with the native or bioprosthetic valve commissure or the valve leaflet at a desired angle,
wherein the projections are loop-shaped projections.

10. A medical device for delivery of a transcatheter heart valve (THV) to a subject, the device comprising:
an elongated member;
a THV
an accessory for receiving the THV thereon and extending from a distal portion of the elongated member, the accessory comprising a plurality of radially outwardly extending projections configured and spaced to align with a leaflet or a commissure of a native or bioprosthetic valve and disposed distally and spaced apart from the THV during delivery of the THV for alignment of the THV with respect to a native or bioprosthetic valve commissure or a valve leaflet at a desired angle during delivery of the THV and wherein the radially outwardly extending projections are spaced apart from the THV, and
a rotational member connected to the elongated member to rotate the accessory and THV together to align with the native or bioprosthetic valve commissure or the valve leaflet at a desired angle,
wherein the projections are configured to extend from the elongated member and retract within the elongated member.

11. A method for delivery of a transcatheter heart valve (THV) to a subject comprising:
providing an elongated member for receiving the THV thereon and having an accessory extending from the distal portion thereof, the accessory comprising a plurality of radially outwardly extending projections disposed at a distal portion of the THV and spaced apart therefrom, the elongated member and accessory housed within and independently rotatable with respect to a delivery catheter;
deploying the elongated member and THV from the delivery catheter at the native valve location;
extending the projections from the elongated member;
rotating the accessory to align the THV with respect to a native or bioprosthetic valve commissure or a valve leaflet at a desired angle; and
expanding the THV in the valve location.

12. The method of claim 11, further comprising, prior to deploying the elongated member, compressing the projections within the delivery catheter into a compressed configuration.

13. The method of claim 12, further comprising, after compressing the projections, advancing the projections to expand to a radially outward configuration.

14. The method of claim 11, wherein the valve location is the aortic valve, the mitral valve, or the tricuspid valve.

15. The method of claim 11, wherein rotating the accessory comprises rotating the accessory to align the radially outwardly extending projections with the native or bioprosthetic valve commissure.

16. The method of claim 11, wherein rotating the accessory comprises rotating the accessory such that the radially outwardly extending projections straddle the native or bioprosthetic valve commissure.

17. The medical device of claim 11, further comprising providing a nose cone positioned distal of the accessory.

18. A method for delivery of a transcatheter heart valve (THV) to a subject comprising:
providing an elongated member for receiving the THV thereon and having an accessory extending from the distal portion thereof, the accessory comprising a plurality of radially outwardly extending projections disposed at a distal portion of the THV and spaced apart therefrom, the elongated member and accessory housed within and independently rotatable with respect to a delivery catheter;
deploying the elongated member and THV from the delivery catheter at the native valve location;

retracting the projections into the elongated member;
rotating the accessory to align the THV with respect to a native or bioprosthetic valve commissure or a valve leaflet at a desired angle; and
expanding the THV in the valve location.

\* \* \* \* \*